United States Patent
Han et al.

(10) Patent No.: US 9,006,294 B2
(45) Date of Patent: Apr. 14, 2015

(54) ORAL PHARMACEUTICAL FORMULATION OF PELUBIPROFEN WITH IMPROVED DISSOLUTION RATE AND STABILITY

(75) Inventors: Joungmin Han, Hwaseong-si (KR); Chankyu Jeoung, Hwaseong-si (KR); Sehhyon Song, Hwaseong-si (KR); Se-il Sohn, Hwaseong-si (KR)

(73) Assignee: Daewon Pharm., Co., Ltd., Seoul (KR)

( * ) Notice: Subject to any disclaimer, the term of this patent is extended or adjusted under 35 U.S.C. 154(b) by 315 days.

(21) Appl. No.: 13/126,277

(22) PCT Filed: Nov. 11, 2009

(86) PCT No.: PCT/KR2009/006619
§ 371 (c)(1),
(2), (4) Date: Apr. 27, 2011

(87) PCT Pub. No.: WO2010/056039
PCT Pub. Date: May 20, 2010

(65) Prior Publication Data
US 2011/0206762 A1    Aug. 25, 2011

(30) Foreign Application Priority Data
Nov. 12, 2008 (KR) ........................ 10-2008-0112295

(51) Int. Cl.
*A61K 31/19* (2006.01)
*A61K 9/14* (2006.01)
*A61K 31/192* (2006.01)
*A61K 9/20* (2006.01)

(52) U.S. Cl.
CPC ............. *A61K 31/192* (2013.01); *A61K 9/2018* (2013.01); *A61K 9/2054* (2013.01)

(58) Field of Classification Search
None
See application file for complete search history.

(56) References Cited

U.S. PATENT DOCUMENTS

| | | | |
|---|---|---|---|
| 2002/0003179 A1* | 1/2002 | Verhoff et al. | ................. 241/21 |
| 2007/0116729 A1 | 5/2007 | Palepu | |
| 2008/0176822 A1 | 7/2008 | Chen | |

FOREIGN PATENT DOCUMENTS

| | | |
|---|---|---|
| JP | 1979-032460 A | 3/1979 |
| JP | 1986-022043 A | 1/1986 |
| JP | 2007-297385 A | 11/2007 |
| KR | 10-2004-0002890 A | 7/2004 |
| WO | 01/41760 A2 | 6/2001 |
| WO | 2007/129169 A2 | 11/2007 |
| WO | WO 2007129169 A2 * 11/2007 ............. A61P 15/08 |

OTHER PUBLICATIONS

Sinha et al., "Binders for colon specific drug delivery: an in vitro evaluation", 2002, International Journal of Pharmaceutics, vol. 249, pp. 23-31.*

* cited by examiner

Primary Examiner — Michael B Pallay
(74) Attorney, Agent, or Firm — Lucas & Mercanti, LLP

(57) ABSTRACT

Disclosed is an oral pharmaceutical formulation of pelubiprofen which is improved in dissolution rate and stability. As a result of an improvement in the dissolution rate of pelubiprofen, the oral pharmaceutical formulation can show high bioavailability and thus exert pharmacological effects thereof rapidly. It also can be stored with high stability as a result of the minimal generation of related compounds.

14 Claims, No Drawings

ORAL PHARMACEUTICAL FORMULATION OF PELUBIPROFEN WITH IMPROVED DISSOLUTION RATE AND STABILITY

CROSS-REFERENCE TO RELATED APPLICATIONS

This application is a 371 of PCT/KR2009/006619 filed on Nov. 11, 2009, which claims the benefit of Korean Patent Application No. 10-2008-0112295 filed on Nov. 12, 2008, the contents of each of which are incorporated herein by reference.

TECHNICAL FIELD

The present invention relates to an oral pharmaceutical formulation improved in dissolution rate and stability, comprising pelubiprofen with a mean particle size of from 1 to 30 µm.

BACKGROUND ART

Pelubiprofen, represented by the following Chemical Formula 1, (molecular formula: $C_{16}H_{18}O_3$, Mw: 258.31, IUPAC Name: 2-[4-(2-oxocyclohexylidenemethyl)phenyl]propionic acid) is a kind of non-steroidal anti-inflammatory drugs (NSAIDs), derived from cycloalkylidenemethyl phenylacetic acid. NSAIDs show various pharmacological effects including anti-inflammatory, analgesic and antipyretic activities. Pelubiprofen is known to show higher pharmacological effects than the current commercial NSAIDs such as loxoprofen, ketoprofen, ibuprofen, and naproxen.

<Chemical Formula 1>

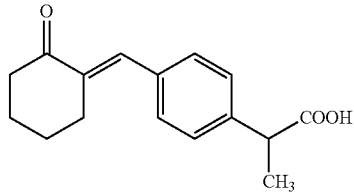

In this regard, pelubiprofen is disclosed in Japanese Patent No. 1167548 (Japanese Patent Application No. 1977-98121) and the preparation method of pelubiprofen is described in Japanese Patent No. 1637767 (Japanese Patent Application No. 1984-142567).

However, the above Japanese patents give only a mere description of pelubiprofen as a novel compound and the synthesis thereof, respectively, but do not elucidate the specific pharmaceutical formulations of pelubiprofen that is applicable to the body, particularly with regard to oral pharmaceutical formulations.

Korean Patent Publication No. 10-2004-0002890 discloses a percutaneously absorbable patch which is improved in both percutaneous absorption and stability of an anti-inflammatory agent in form of a salt. A sodium salt of pelubiprofen is introduced as an anti-inflammatory agent in the form of a salt.

But, the pharmaceutical formulation disclosed in the Korean Patent is a percutaneously absorbable patch, not an oral pharmaceutical formulation, and the used pelubiprofen is a salt form.

Dosage form design is prerequisite for the application of drugs to the body. "Dosage form design" usually refers to determining optimal pharmaceutical formulation and a dosage regimen which meet optimal conditions for chemical and physical properties, pharmacological actions and therapeutic purposes. In order to exert pharmacological effects thereof, a chemical compound should be formulated into specific forms, such as tablets, capsules, injections, ointments, pastes, etc. Also, the properties of a designed formulation should be supported by concrete experimentation using the dosage forms of the chemical.

Usually, NSAIDs are required to exert the pharmacological effects thereof rapidly. In this context, NSAIDs have been developed as injection formulations, such as subcutaneous and intravenous injections as found in the market. Although advantageous in that their effects are rapid, the injection formulations impart a limitation on their administration.

One of the prerequisites for the development of NSAIDs is a dissolution rate which is high enough to allow them to rapidly exert their pharmacological effects. Typically, improving the dissolution rate of oral pharmaceutical formulations may be achieved by 1) milling particles of active ingredients into small sizes, 2) adding surfactants, 3) atomizing the formulation to nano-sizes, or 4) employing a solid dispersant.

On the whole, the smaller the active ingredient particles are in size, the better the dissolution rates thereof are. Smaller particle sizes of the active ingredients increase the surface areas thereof, however, they result in a greater opportunity to react with the other additives contained in the oral formulation and in turn decrease the stability of the active ingredients.

As such, many different additives other than the active ingredient in an oral pharmaceutical formulation may be more apt to deteriorate the pharmaceutical effects of the active ingredient when its size is smaller. In order to solve this problem, the present inventors have studied the stabilization of oral pharmaceutical formulations with convenience and effectiveness in mind.

Leading to the present invention, intensive and thorough research, conducted by the present inventors, into an oral pharmaceutical formulation of pelubiprofen which has a high dissolution rate with a concomitant maintenance of stability, resulted in the finding that a pelubiprofen particle size ranging from 1 to 30 µm in combination with specific additives greatly improves the dissolution rate and stability of the oral pharmaceutical formulation thereof.

DISCLOSURE OF INVENTION

Technical Problem

It is therefore an object of the present invention to provide an oral pharmaceutical formulation of pelubiprofen which is improved in dissolution rate and stability and can rapidly exert pharmacological effects as well as which is easy to prepare.

Technical Solution

In order to achieve the object, the present invention provides an oral pharmaceutical formulation comprising pelubiprofen represented by the following chemical formula 1 as an active ingredient and one or more pharmaceutically acceptable expedients, wherein pelubiprofen has a mean particle size of from 1 to 30 µm and the said one or more pharmaceutically acceptable expedients are selected from a group consisting of a diluent selected from a group consisting of lactose, calcium phosphate, starch, polyol and a combination thereof;

a binder selected from a group consisting of hydroxypropyl cellulose, polysaccharide and a combination thereof;
a disintegrator selected from a group consisting of carboxymethyl cellulose calcium, low-substituted hydroxypropyl cellulose, starch and a combination thereof;
a lubricant selected from a group consisting of magnesium stearate, talc and a combination thereof;
and a combination thereof.

<Chemical Formula 1>

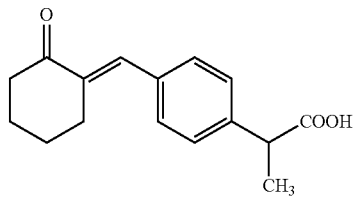

Advantageous Effects

The oral pharmaceutical formulation of the present invention can show high bioavailability and thus exert pharmacological effects thereof rapidly as a result of an improvement in the dissolution rate of pelubiprofen and can be stored stable as a result of the minimal generation of related compounds.

BEST MODE FOR CARRYING OUT THE INVENTION

The present invention provides an oral pharmaceutical formulation, improved in dissolution rate and stability, comprising pelubiprofen having a mean particle size of from 1 to 30 μm as an active ingredient.

The present invention provides, in detail, an oral pharmaceutical formulation comprising pelubiprofen as an active ingredient and one or more pharmaceutically acceptable expedients, wherein pelubiprofen has a mean particle size of from 1 to 30 μm and the said one or more pharmaceutically acceptable expedients are selected from a group consisting of a diluent selected from a group consisting of lactose, calcium phosphate, starch, polyol and a combination thereof; a binder selected from a group consisting of hydroxypropyl cellulose, polysaccharide and a combination thereof; a disintegrator selected from a group consisting of carboxymethyl cellulose calcium, low-substituted hydroxypropyl cellulose, starch and a combination thereof; a lubricant selected from a group consisting of magnesium stearate, talc and a combination thereof; and a combination thereof.

Pelubiprofen, an active ingredient of the oral pharmaceutical formulation in accordance with the present invention, is represented by the following chemical formula 1.

<Chemical Formula 1>

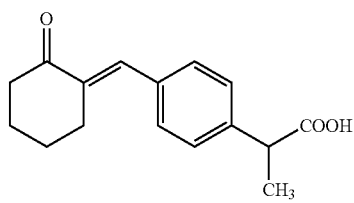

Pelubiprofen is a chemical compound having the IUPAC name of 2-[4-(2-oxocyclohexylidenemethyl)phenyl]propionic acid and a molecular formula of $C_{16}H_{18}O_3$ with a molecular weight of 258.31, known to show analgesic and anti-inflammatory effects.

In accordance with the present invention, mean particle size of pelubiprofen preferably ranges from 1 to 30 μm. For example, pelubiprofen particles are difficult to prepare when less than 1 μm in mean particle size, although their dissolution rate increases thanks to the increased surface area thereof. On the other hand, pelubiprofen particles exceeding 30 μm in size have a decreased dissolution rate. Dissolution rates by mean particle sizes of pelubiprofen are given in Table 1, below.

TABLE 1

| mean particle size of pelubiprofen (μm) | dissolution rate (%) |
| --- | --- |
| 9.3 | 85.8 |
| 19.1 | 75.3 |
| 27.4 | 70.4 |
| 45.6 | 41.4 |

Pelubiprofen particles may be grinded finely using a mill suitable for a wet or dry granulation method. So long as it can grind the particles into a mean particle size of 1~30 μm, any mill may be used. Examples of the mill suitable for use in the present invention include a fluid energy mill and a micron mill, but it is not limited thereto.

The oral pharmaceutical formulation in accordance with the present invention may also comprise specific amounts of additives such as diluents, binders, disintegrators, and lubricants. These additives may be preferably selected from those described below in the context that they can reduce the generation of related compounds when used in combination with the active ingredient pelubiprofen.

As diluents, lactose, calcium phosphate, starch, and polyol are preferably used. Preferred examples of the polyol include mannitol, isomalt and xylitol. Preferably, the binder may be selected from among hydroxypropyl cellulose and polysaccharides. Preferred examples of the polysaccharides include xanthan gum and carrageenan. Preferred disintegrators useful in the present invention may be exemplified by carboxymethyl cellulose calcium, low-substituted hydroxypropyl cellulose, and starch. Magnesium stearate and talc are preferred over other lubricants.

When pelubiprofen was used in combination with the above-mentioned diluents, binders, disintegrators and lubricants, the minimum amount of the related compounds was generated.

The selectivity described above is related to the particle size of pelubiprofen. Even other additives in the formulation have insignificant effects on the generation of related compounds when the mean particle size of pelubiprofen is over 30 μm. In contrast, the related compounds are generated in large amounts, decreasing the stability when a solubilizer is used to increase the dissolution rate of the formulation. But, pelubiprofen with a mean particle size of from 1 to 30 μm in combination with the additives in accordance with the present invention shows high dissolution rates without the need of any solubilizer. In addition, the formulation is stable because almost no related compounds are additionally generated even in the presence of the additives, such as diluents, binders, disintegrators, lubricants, etc.

Increased amounts of related compounds were measured after oral pharmaceutical formulations with different mean particle sizes (27.4 μm, 45.6 μm) of pelubiprofen in combination with different amounts of various additives were stored for two weeks under the severe condition of 60° C. The results are summarized in Table 2, below.

TABLE 2

| MPS[1] of Pelubiprofen (μm) | Pelubiprofen (mg) | Additive | | Total Related Cpd. (%) | Increase of Related Cpd. (%) |
|---|---|---|---|---|---|
| 27.4 | 20 | | None | 0.461 | 9.5 |
| | | Diluent (60) | Lactose | 0.452 | 7.4 |
| | | | MCC[2] | 1.124 | 167.0 |
| | | | MgCO$_3$ | 1.568 | 272.4 |
| | | | CMC[3] | 1.012 | 140.4 |
| | | | calcium phosphate | 0.457 | 8.6 |
| | | | PGS[4] | 0.457 | 8.6 |
| | | | Mannitol | 0.451 | 7.1 |
| | | | Isomalt | 0.458 | 8.8 |
| | | | Xylitol | 0.461 | 9.5 |
| | | Binder (10) | HPC[5] | 0.458 | 8.8 |
| | | | Povidone | 3.421 | 712.6 |
| | | | HPMC[6] | 1.940 | 360.8 |
| | | | Xanthan gum | 0.455 | 8.1 |
| | | | CGN[7] | 0.461 | 9.5 |
| | | | CMC Na[8] | 1.770 | 320.4 |
| | | Dis-integrator (10) | CMC Ca[9] | 0.456 | 8.3 |
| | | | L-HPC[10] | 0.452 | 7.4 |
| | | | Corn starch | 0.454 | 7.8 |
| | | | Crospovidone | 1.238 | 194.1 |
| | | | Croscarmellose Na | 1.405 | 233.7 |
| | | Lubricant (5) | Mg Stearate | 0.458 | 8.8 |
| | | | Talc | 0.460 | 9.3 |
| | | | GB[11] | 1.245 | 195.7 |
| | | | CSD[12] | 1.357 | 222.3 |
| | | | Stearic acid | 2.215 | 426.1 |
| | | Solubilizer (5) | POES[13] | 3.012 | 615.4 |
| | | | SLS[14] | 2.568 | 510.0 |
| | | | Polysorbate | 3.425 | 713.5 |
| | | | Poloxamer | 4.014 | 853.4 |
| 45.6 | 20 | | None | 0.432 | 2.6 |
| | | Diluent (60) | Lactose | 0.441 | 4.8 |
| | | | MCC[2] | 0.454 | 7.8 |
| | | | MgCO$_3$ | 0.462 | 9.7 |
| | | | calcium phosphate | 0.439 | 4.3 |
| | | | Mannitol | 0.443 | 5.2 |
| | | Binder (10) | HPC[5] | 0.445 | 5.7 |
| | | | Povidone | 0.458 | 8.8 |
| | | | HPMC[6] | 0.442 | 5.0 |
| | | | CMC Na[8] | 0.445 | 5.7 |
| | | Dis-integrator (10) | CMC Ca[9] | 0.439 | 4.3 |
| | | | L-HPC[10] | 0.438 | 4.0 |
| | | | Corn starch | 0.442 | 5.0 |
| | | | Crospovidone | 0.458 | 8.8 |
| | | Lubricant (5) | Mg stearate | 0.438 | 4.0 |
| | | | Talc | 0.442 | 5.0 |
| | | | GB[11] | 0.445 | 5.7 |
| | | | CSD[12] | 0.447 | 6.2 |
| | | Solubilizer (5) | POES[13] | 2.203 | 423.3 |
| | | | SLS[14] | 1.962 | 366.0 |

Note:
[1]Mean Particle Size
[2]Microcrystalline cellulose
[3]Carboxymethyl cellulose
[4]Pre-gelatinized starch
[5]Hydroxypropyl cellulose
[6]Hydroxypropylmethyl cellulose
[7]Carrageenan
[8]Carboxymethyl cellulose sodium
[9]Carboxymethyl cellulose calcium
[10]low-substituted hydroxypropyl cellulose
[11]Glyceryl behenate
[12]Colloidal silicon dioxide
[13]Polyoxyethylene stearates
[14]Sodium lauryl sulfate As concerns the amount of the additives, it preferably ranges from 0.5 to 50 parts by weight for the diluent, from 0.00125 to 2.5 parts by weight for the binder, from 0.00125 to 20 parts by weight for the disintegrator, and from 0.00125 to 2.5 parts by weight for the lubricant, based on 1 part by weight of pelubiprofen.

A content of the diluent less than 0.5 parts by weight makes it difficult to form tablets while a content greater than 50 parts encroaches the content of the active ingredient. When the binder is used in an amount less than 0.00125 parts by weight, the tablet may be rendered fragile due to low hardness. On the other hand, when the binder is used in an amount greater than 2.5 parts by weight, the dissolution rate of the oral formulation is low. With a content of the disintegrator less than 0.00125 parts by weight, the oral pharmaceutical formulation barely disintegrates. When the content exceeds 20 parts by weight, the oral pharmaceutical formulation absorbs too much moisture during storage to be stable. Turning to the lubricant, it may have a negative influence on fluidity and cause significant weight deviations of the formulation when its amount is less than 0.00125 parts by weight, and may make it difficult to form tablets and may be likely to delay dissolution when is present in excess of 2.5 parts by weight.

From the point of view of improving the dissolution rate of the active ingredient and suppressing the increase rate of related compounds, a preferred embodiment of the present invention provides an oral pharmaceutical formulation comprising pelubiprofen having a mean particle size of from 1 to 30 μm as an active ingredient in combination with lactose as a diluents hydroxypropyl cellulose as a binder carboxymethyl cellulose calcium, low-substituted hydroxypropyl cellulose or a mixture thereof as a disintegrator; and magnesium stearate as a lubricant.

The oral pharmaceutical formulation according to the present invention may be prepared using a typical method known therefor.

For the purpose of the convenience of administration, the oral pharmaceutical formulation of the present invention may preferably be in the form of tablets. However, powders, capsules, granules, syrups and other oral formulations may be taken in terms of immediate pharmacological effect and effective biological availability. Various solid formulations for oral administration may be prepared with the expedients of the present invention using typical methods.

MODE FOR THE INVENTION

A better understanding of the present invention may be obtained through the following examples which are set forth to illustrate, but are not to be construed as limiting the present invention.

EXAMPLE 1

2.1 g of hydroxypropyl cellulose was added to 34.3 mL of purified water to produce a binder solution. Separately, 30 g of pelubiprofen with a mean particle size of 9.3 μm was mixed with 47.9 g of lactose, 10 g of carboxymethyl cellulose calcium and 18 g of low-substituted hydroxypropyl cellulose. This mixture was combined with the binder solution, granulated and dried, followed by filtering the granules through an 18-mesh sieve. The filtered granules were mixed with 1.9 g of magnesium stearate.

EXAMPLES 2 TO 20

The same procedure as in Example 1 was repeated with the exception that the mean particle sizes of pelubiprofen and the kinds and content of the additives were varied as indicated in Table 3, below.

TABLE 3

| Ex. | MPS[1] of Pelubiprofen (μm) | Pelubiprofen (g) | Diluent (g) | Binder (g) | Disintegrator (g) | Lubricant (g) |
|---|---|---|---|---|---|---|
| 1 | 9.3 | 30 | Lactose (47.9) | HPC[2] (2.1) | CMC Ca[3] (10)   L-HPC[4] (18) | Mg Stearate (1.9) |
| 12 |  | 30 | Lactose (57.9) | Xanthan gum (2.1) | L-HPC[4] (18) | Talc (1.9) |
| 3 |  | 30 | calcium phosphate (57.9) | HPC[2] (2.1) | L-HPC[4] (18) | Mg Stearate (1.9) |
| 4 |  | 30 | calcium phosphate (57.9) | CGN[5] (2.1) | CMC Ca[3] (18) | Talc (1.9) |
| 5 |  | 30 | PGS[6] (57.9) | HPC[2] (2.1) | CMC Ca[3] (18) | Mg Stearate (1.9) |
| 6 |  | 30 | PGS[6] (57.9) | Xanthan gum (2.1) | L-HPC[4] (18) | Talc (1.9) |
| 7 |  | 30 | Mannitol (57.9) | HPC[2] (2.1) | Corn starch (18) | Mg Stearate (1.9) |
| 8 |  | 30 | Mannitol (57.9) | Xanthan gum (2.1) | L-HPC[4] (18) | Talc (1.9) |
| 9 |  | 30 | Isomalt (47.9) | HPC[2] (2.1) | CMC Ca[3] (10)   L-HPC[4] (18) | Mg Stearate (1.9) |
| 10 |  | 30 | Isomalt (57.9) | CGN[5] (2.1) | Corn starch (18) | Talc (1.9) |
| 11 |  | 30 | Xylitol (57.9) | Xanthan gum (2.1) | CMC Ca[3] (18) | Mg Stearate (1.9) |
| 12 |  | 30 | Xylitol (57.9) | HPC[2] (2.1) | Corn starch (18) | Talc (1.9) |
| 13 | 19.1 | 30 | Lactose (57.9) | Xanthan gum (2.1) | L-HPC[4] (18) | Talc (1.9) |
| 14 |  | 30 | calcium phosphate (57.9) | CGN[5] (2.1) | CMC Ca[3] (18) | Talc (1.9) |
| 15 |  | 30 | Mannitol (57.9) | HPC[2] (2.1) | Corn starch (18) | Mg Stearate (1.9) |

TABLE 3-continued

| Ex. | MPS[1] of Pelubi-profen (μm) | Pelubi-profen (g) | Diluent (g) | Binder (g) | Disintegrator (g) | Lubricant (g) |
|---|---|---|---|---|---|---|
| 16 | | 30 | Xylitol (57.9) | Xanthan gum (2.1) | CMC Ca[3] (18) | Mg Stearate (1.9) |
| 17 | 27.4 | 30 | Lactose (57.9) | Xanthan gum (2.1) | L-HPC[4] (18) | Talc (1.9) |
| 18 | | 30 | calcium phosphate (57.9) | CGN[5] (2.1) | CMC Ca[3] (18) | Talc (1.9) |
| 19 | | 30 | Mannitol (57.9) | HPC[2] (2.1) | Corn starch (18) | Mg Stearate (1.9) |
| 20 | | 30 | Xylitol (57.9) | Xanthan gum (2.1) | CMC Ca[3] (18) | Mg Stearate (1.9) |

NOTE:
[1] Mean particle size
[2] Hydroxypropyl cellulose
[3] Carboxymethyl cellulose calcium
[4] Low-substituted hydroxypropyl cellulose
[5] Carrageenan
[6] Pre-gelatinized starch

COMPARATIVE EXAMPLES 1 TO 18

The same procedure as in Example 1 was repeated except that the mean particle size of pelubiprofen and the kinds and content of the additives were varied as indicated in Table 4, below.

TABLE 4

| Ex. | MPS[1] of Pelubi-profen (μm) | Pelubi-profen (g) | Diluent (g) | Binder (g) | Disintegrator (g) | Lubricant (g) | Solubilizer (g) |
|---|---|---|---|---|---|---|---|
| 1 | 45.6 | 30 | Lactose (57.9) | Xanthan gum (2.1) | L-HPC[2] (18) | Talc (1.9) | — |
| 2 | | 30 | calcium phosphate (57.9) | CGN[3] (2.1) | CMC Ca[4] (18) | Talc (1.9) | — |
| 3 | | 30 | Mannitol (57.9) | HPC[5] (2.1) | Corn starch (18) | Mg St[9] (1.9) | — |
| 4 | | 30 | Xylitol (57.9) | Xanthan gum (2.1) | CMC Ca[4] (18) | Mg St[9] (1.9) | — |
| 5 | 27.4 | 30 | MCC[6] (57.9) | HPC[5] (2.1) | Corn starch (18) | Mg St[9] (1.9) | — |
| 6 | | 30 | MgCO$_3$ (57.9) | Xanthan gum (2.1) | L-HPC[2] (18) | Talc (1.9) | — |
| 7 | | 30 | CMC[8] (57.9) | CGN[3] (2.1) | L-HPC[2] (18) | Mg St[9] (1.9) | — |
| 8 | | 30 | Lactose (57.9) | Povidone (2.1) | L-HPC[2] (18) | Talc (1.9) | — |
| 9 | | 30 | calcium phosphate (57.9) | HPMC[16] (2.1) | Crospovidone (18) | Mg St[9] (1.9) | — |
| 10 | | 30 | Isomalt (57.9) | CMC Na[7] (2.1) | Corn starch (18) | Talc (1.9) | — |
| 11 | | 30 | Mannitol (57.9) | CGN[3] (2.1) | CC Na[14] (18) | Mg St[9] (1.9) | — |
| 12 | | 30 | Lactose (57.9) | HPC[5] (2.1) | L-HPC[2] (18) | Stearic acid (1.9) | — |
| 13 | | 30 | PGS[15] (57.9) | Xanthan gum (2.1) | CMC Ca[4] (18) | CSD[10] (1.9) | — |
| 14 | | 30 | Isomalt (57.9) | HPC[5] (2.1) | Corn starch (18) | GB[11] (1.9) | — |
| 15 | 27.4 | 30 | Lactose (57.9) | Xanthan gum (2.1) | L-HPC[2] (18) | Talc (1.9) | POES[12] (10) |
| 16 | | 30 | calcium phosphate (57.9) | CGN[3] (2.1) | CMC Ca[1] (18) | Talc (1.9) | SLS[13] (10) |
| 17 | | 30 | Mannitol (57.9) | HPC[5] (2.1) | Corn starch (18) | Mg St[9] (1.9) | Polysorbate (10) |

TABLE 4-continued

| Ex. | MPS[1] of Pelubi-profen (μm) | Pelubi-profen (g) | Diluent (g) | Binder (g) | Disintegrator (g) | Lubricant (g) | Solubilizer (g) |
|---|---|---|---|---|---|---|---|
| 18 | | 30 | Xylitol (57.9) | Xanthan gum (2.1) | CMC Ca[4] (18) | Mg St[9] (1.9) | Poloxamer (10) |

NOTE:
[1]Mean particle size
[2]Low-substituted hydroxypropyl cellulose
[3]Carrageenan
[4]Carboxymethyl cellulose calcium
[5]Hydroxypropyl cellulose
[6]Microcrystalline cellulose
[7]Carboxymethyl cellulose sodium
[8]Carboxymethyl cellulose
[9]Magnesium stearate
[10]Colloidal silicon dioxide
[11]Glyceryl behenate
[12]Polyoxyethylene stearates
[13]Sodium lauryl sulfate
[14]Croscarmellose sodium
[15]Pre-gelatinized Starch
[16]Hydroxypropylmethyl cellulose

TEST EXAMPLE 1

Dissolution Rates of Oral Pharmaceutical Formulations of Pelubiprofen

Pelubiprofen tablets differing in the mean particle size of pelubiprofen and the kinds and content of additives were measured for dissolution rate as follows.

A dissolution test was performed on the pelubiprofen tablets prepared in Examples 1 to 20 and Comparative Examples 1 to 18.

The dissolution test was performed according to the procedure of Paddle Method described in Korean Pharmacopoeia. In this regard, one tablet was tested in 900 mL of a dissolution medium (pH 1.2) at 37±0.5° C., with a maintenance of paddle rotation speed at 50 rpm. After a 45-min test, the dissolution medium was taken and filtered through a 0.45 μm filter, followed by the UV analysis of the filtrate. The results are shown in Table 5, below.

TABLE 5

| Example | Dissolution Rate (%) | Comparative Example | Dissolution Rate (%) |
|---|---|---|---|
| 1 | 85.8 | 1 | 40.4 |
| 2 | 84.4 | 2 | 40.1 |
| 3 | 84.7 | 3 | 39.2 |
| 4 | 82.1 | 4 | 39.9 |
| 5 | 81.0 | 5 | 62.3 |
| 6 | 85.2 | 6 | 61.2 |
| 7 | 82.2 | 7 | 60.8 |
| 8 | 82.6 | 8 | 62.1 |
| 9 | 81.9 | 9 | 60.4 |
| 10 | 81.7 | 10 | 61.4 |
| 11 | 82.6 | 11 | 63.0 |
| 12 | 81.4 | 12 | 61.2 |
| 13 | 75.3 | 13 | 60.1 |
| 14 | 74.1 | 14 | 60.1 |
| 15 | 72.0 | 15 | 95.2 |
| 16 | 73.3 | 16 | 92.5 |
| 17 | 70.4 | 17 | 91.4 |
| 18 | 70.2 | 18 | 91.5 |
| 19 | 71.0 | — | — |
| 20 | 70.2 | — | — |

As is apparent from the data of Table 5, the use of pelubi-profen of not more than 30 μm in mean particle size in combination with specific additives guarantees a dissolution rate of 70% or higher. However, a dissolution rate as low as about 40% was measured when pelubiprofen particles were of a mean particle size larger than 45.6 μm as in Comparative Examples 1 to 4. In addition, Comparative Examples 5 to 18 which were conducted with pelubiprofen of less than 30 μm in mean particle size still showed dissolution rates less than 70% when certain additives such as microcrystalline cellulose, magnesium carbonate, carboxymethyl cellulose and povidone were employed.

Accordingly, the data demonstrate that the use of pelubi-profen having a mean particle size of from 1 to 30 μm in combination with specific additives ensures a high dissolution rate for the oral pharmaceutical formulation.

TEST EXAMPLE 2

Increased Rate of Related Compounds in Oral Pharmaceutical Formulations of Pelubiprofen The stabilities of oral pharmaceutical formulations depending on additives were tested as follows.

The tablets prepared in Examples 1 to 20 and Comparative Examples 5 to 18 were stored for two weeks under the severe condition of 60° C. Thereafter, they were quantitatively measured for total related compounds and the increase rates of related compounds are shown in Table 6, below.

TABLE 6

| Example | Increase of Related Cpd. (%) | Comparative Example | Increase of Related Cpd. (%) |
|---|---|---|---|
| 1 | 5.2 | 5 | 164.2 |
| 2 | 5.2 | 6 | 169.2 |
| 3 | 5.4 | 7 | 137.2 |
| 4 | 7.3 | 8 | 709.4 |
| 5 | 7.1 | 9 | 357.5 |
| 6 | 5.4 | 10 | 317.2 |
| 7 | 6.3 | 11 | 230.5 |
| 8 | 6.4 | 12 | 412.9 |
| 9 | 6.0 | 13 | 219.0 |
| 10 | 6.6 | 14 | 192.4 |
| 11 | 7.1 | 15 | 610.1 |
| 12 | 5.0 | 16 | 505.2 |
| 13 | 7.0 | 17 | 709.9 |

TABLE 6-continued

| Example | Increase of Related Cpd. (%) | Comparative Example | Increase of Related Cpd. (%) |
|---|---|---|---|
| 14 | 5.2 | 18 | 848.2 |
| 15 | 5.4 | — | — |
| 16 | 6.6 | — | — |
| 17 | 6.3 | — | — |
| 18 | 6.4 | — | — |
| 19 | 7.0 | — | — |
| 20 | 6.9 | — | — |

As is understood from the data of Table 6, almost no increases were detected in the amounts of the related compounds when pelubiprofen with a mean particle size of 30 μm or less was used in combination with specific additives, but an increase rate of as high as 150% was measured in the presence of microcrystalline cellulose, magnesium carbonate, carboxymethyl cellulose and povidone as in Comparative Examples 5 to 18.

From the data, it is demonstrated that the additives selected according to the present invention reduced the generation of related compounds to a minimum level, guaranteeing the stability of the oral pharmaceutical formulation even upon storage for a long period of time.

INDUSTRIAL APPLICABILITY

As described above, the oral pharmaceutical formulation of pelubiprofen in accordance with the present invention overcomes the problems, encountered in the prior art, of low dissolution rate and stability, making a great contribution to the commercialization of pelubiprofen drugs.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An oral pharmaceutical formulation comprising pelubiprofen represented by chemical formula 1 as an active ingredient and pharmaceutically acceptable additives,

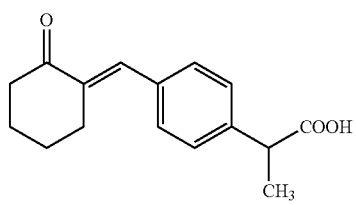

<Chemical Formula 1> wherein
the pelubiprofen has a mean particle size of from 1 to 30 μm and the pharmaceutically acceptable additives comprise:
a diluent selected from the group consisting of lactose, calcium phosphate, starch, mannitol, isomalt, xylitol and a combination thereof in an amount of from 0.5 to 50 parts by weight of pelubiprofen;
a binder selected from the group consisting of hydroxypropyl cellulose, xanthan gum, carrageenan and a combination thereof in an amount of from 0.00125 to 2.5 parts by weight of pelubiprofen;
a disintegrator selected from the group consisting of carboxymethyl cellulose calcium, low-substituted hydroxypropyl cellulose, starch and a combination thereof in an amount of from 0.00125 to 20 parts by weight of pelubiprofen; and
a lubricant selected from the group consisting of magnesium stearate, talc and a combination thereof in an amount of from 0.00125 to 2.5 parts by weight of pelubiprofen.

2. The oral pharmaceutical formulation of claim 1 wherein
the diluent is selected from the group consisting of lactose, calcium phosphate and starch;
the binder is selected from the group consisting of hydroxypropyl cellulose and xanthan gum;
the disintegrator is selected from the group consisting of carboxymethyl cellulose calcium and low-substituted hydroxypropyl cellulose; and
the lubricant is selected from the group consisting of magnesium stearate and talc.

3. The oral pharmaceutical formulation of claim 1, wherein the oral pharmaceutical formulation is in a form of a tablet.

4. The oral pharmaceutical formulation of claim 1, wherein the oral pharmaceutical formulation exhibits less than a 7.4% increase of related compounds after 2 weeks when stored at 60° C.

5. The oral pharmaceutical formulation according to claim 1, wherein the oral pharmaceutical formulation exhibits more than a 70% dissolution rate after a 45 minute test when tested in 900 mL of a dissolution medium having pH 1.2 at 37±0.5° C., with a maintenance of paddle rotation speed at 50 rpm.

6. An oral pharmaceutical formulation consisting essentially of:
pelubiprofen represented by chemical formula 1 as an active ingredient,

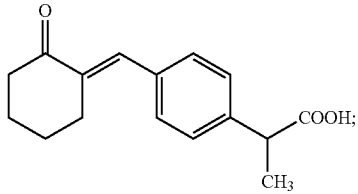

<Chemical Formula 1> a diluent selected from the group consisting of lactose, calcium phosphate, starch, mannitol, isomalt, xylitol and a combination thereof in an amount of from 0.5 to 50 parts by weight of pelubiprofen;
a binder selected from the group consisting of hydroxypropyl cellulose, xanthan gum, carrageenan and a combination thereof in an amount of from 0.00125 to 2.5 parts by weight of pelubiprofen;
a disintegrator selected from the group consisting of carboxymethyl cellulose calcium, low-substituted hydroxypropyl cellulose, starch and a combination thereof in an amount of from 0.00125 to 20 parts by weight of pelubiprofen; and
a lubricant selected from the group consisting of magnesium stearate, talc and a combination thereof in an amount of from 0.00125 to 2.5 parts by weight of pelubiprofen,
wherein, the pelubiprofen has a mean particle size of from 1 to 30 μm.

7. The oral pharmaceutical formulation of claim 6, wherein the oral pharmaceutical formulation is in a form of a tablet.

8. The oral pharmaceutical formulation of claim 6, wherein the oral pharmaceutical formulation exhibits less than a 7.4% increase of related compounds after 2 weeks when stored at 60° C.

9. The oral pharmaceutical formulation according to claim 6, wherein the oral pharmaceutical formulation exhibits more than a 70% dissolution rate after a 45 minute test when tested in 900 mL of a dissolution medium having pH 1.2 at 37±0.5° C., with a maintenance of paddle rotation speed at 50 rpm.

10. An oral pharmaceutical formulation for anti-inflammatory drugs comprising:
pelubiprofen represented by the following chemical formula 1 as an active ingredient and a combination of a diluent, a binder, a disintegrator and a lubricant, <Chemical Formula 1>

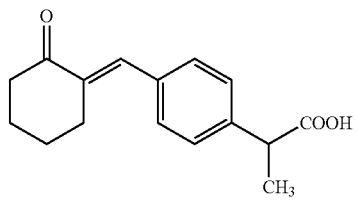

wherein
the pelubiprofen has a mean particle size of from 1 to 30 μm;
the oral pharmaceutical formulation is a tablet; and
the combination of a diluent, a binder, a disintegrator and a lubricant is selected from the group consisting of:
1) the diluent being lactose, the binder being hydroxypropyl cellulose, the disintegrator being a mixture of carboxymethyl cellulose calcium and low-substituted hydroxypropyl cellulose, and the lubricant being magnesium stearate;
2) the diluent being lactose, the binder being xanthan gum, the disintegrator being low-substituted hydroxypropyl cellulose, and the lubricant being talc;
3) the diluent being calcium phosphate, the binder being hydroxypropyl cellulose, the disintegrator being low-substituted hydroxypropyl cellulose, and the lubricant being magnesium stearate;
4) the diluent being calcium phosphate, the disintegrator being carageenan, the disintegrator being carboxymethyl cellulose calcium, and the lubricant being talc;
5) the diluent being pre-gelatinized starch, the binder being hydroxypropyl cellulose, the disintegrator being carboxymethyl cellulose calcium, and the lubricant being magnesium stearate;
6) the diluent being pre-gelatinized starch, the binder being xanthan gum, the disintegrator being low-substituted hydroxypropyl cellulose, and the lubricant being talc;
7) the diluent being mannitol, the binder being hydroxypropyl cellulose, the disintegrator being corn starch, and the lubricant being magnesium stearate;
8) the diluent being mannitol, the binder being xanthan gum, the disintegrator being low-substituted hydroxypropyl cellulose, and the lubricant being talc;
9) the diluent being isomalt, the binder being hydroxypropyl cellulose, the disintegrator being a mixture of carboxymethyl cellulose calcium and low-substituted hydroxypropyl cellulose, and the lubricant being magnesium stearate;
10) the diluent being isomalt, the binder being carageenan, the disintegrator being corn starch, and the lubricant being talc;
11) the diluent being xylitol, the binder being xanthan gum, the disintegrator being carboxymethyl cellulose calcium, and the lubricant being magnesium stearate; and
12) the diluent being xylitol, the binder being hydroxypropyl cellulose, the disintegrator being corn starch, and the lubricant being talc,
wherein
the diluent being in an amount of from 0.5 to 50 parts by weight of pelubiprofen;
the binder being in an amount of from 0.00125 to 2.5 parts by weight of pelubiprofen;
the disintegrator being in an amount of from 0.00125 to 20 parts by weight of pelubiprofen; and
the lubricant being in an amount of from 0.00125 to 2.5 parts by weight of pelubiprofen.

11. The oral pharmaceutical formulation of claim 10, wherein the oral pharmaceutical formulation is in a form of a tablet.

12. The oral pharmaceutical formulation of claim 10, wherein the oral pharmaceutical formulation exhibits less than a 7.4% increase of related compounds after 2 weeks when stored at 60° C.

13. The oral pharmaceutical formulation according to claim 10, wherein the oral pharmaceutical formulation exhibits more than a 70% dissolution rate after a 45 minute test when tested in 900 mL of a dissolution medium having pH 1.2 at 37±0.5° C., with a maintenance of paddle rotation speed at 50 rpm.

14. The oral pharmaceutical formulation of claim 10, wherein the combination consists:
lactose as the diluent;
hydroxypropyl cellulose as the binder;
a mixture of carboxymethyl cellulose calcium and low-substituted hydroxypropyl cellulose as the disintegrator; and
magnesium stearate as the lubricant.

* * * * *